United States Patent
Beymer et al.

(10) Patent No.: US 10,327,712 B2
(45) Date of Patent: Jun. 25, 2019

(54) PREDICTION OF DISEASES BASED ON ANALYSIS OF MEDICAL EXAM AND/OR TEST WORKFLOW

(71) Applicant: International Business Machines Corporation, Armonk, NY (US)

(72) Inventors: David J. Beymer, San Jose, CA (US); Karen W. Brannon, Palo Alto, CA (US); Colin B. Compas, San Jose, CA (US); Ritwik K. Kumar, Sunnyvale, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 578 days.

(21) Appl. No.: 14/540,159

(22) Filed: Nov. 13, 2014

(65) Prior Publication Data

US 2015/0141826 A1    May 21, 2015

Related U.S. Application Data

(60) Provisional application No. 61/905,189, filed on Nov. 16, 2013.

(51) Int. Cl.
*G06G 7/60* (2006.01)
*A61B 5/00* (2006.01)
(Continued)

(52) U.S. Cl.
CPC .......... *A61B 5/7275* (2013.01); *A61B 5/0006* (2013.01); *A61B 5/0022* (2013.01);
(Continued)

(58) Field of Classification Search
CPC .................................. G06K 9/00; G06G 7/60
See application file for complete search history.

(56) References Cited

U.S. PATENT DOCUMENTS 5,889,993 A * 3/1999 Kroeger .............. G06F 12/0862
707/E17.01
6,047,259 A    4/2000 Campbell et al.
(Continued)

FOREIGN PATENT DOCUMENTS

EP    1394715 A1    3/2004
WO    03034287 A1   4/2003
(Continued)

OTHER PUBLICATIONS

Baumgartner et al., "Echocardiographic assessment of valve stenosis: EAE/ASE recommendations for clinical practice", European Journal of Echocardiography (2009) 10, pp. 1-25, doi:10.1093/ejechocard/jen303, Published on behalf of the European Society of Cardiology, All rights reserved, © The Author 2008.
(Continued)

*Primary Examiner* — Victoria P Augustine
*Assistant Examiner* — Chad A Newton
(74) *Attorney, Agent, or Firm* — David B. Woycechowsky

(57) ABSTRACT

Use of medical workflows where a first medical workflow is obtained from a plurality of medical acts performed in sequence that related to care of a patient. A set of condition-indication rules is applied to the first medical workflow to determine first condition information. The first condition information relates to a likelihood that a first medical condition exists in the patient.

3 Claims, 12 Drawing Sheets

(51) Int. Cl.
A61B 8/00 (2006.01)
A61B 8/08 (2006.01)
(52) U.S. Cl.
CPC .......... *A61B 5/7264* (2013.01); *A61B 5/7267* (2013.01); *A61B 8/565* (2013.01); *A61B 8/0883* (2013.01); *A61B 8/488* (2013.01); *A61B 8/5223* (2013.01)

(56) References Cited

U.S. PATENT DOCUMENTS

| | | | |
|---|---|---|---|
| 7,937,277 | B2 | 5/2011 | Marx |
| 8,137,273 | B2 | 3/2012 | Everett et al. |
| 8,463,741 | B2 | 6/2013 | Ehlke et al. |
| 8,548,828 | B1* | 10/2013 | Longmire ............ G06Q 10/10 705/3 |
| 2008/0228685 | A1 | 9/2008 | Shivaji-Rao et al. |
| 2012/0136679 | A1 | 5/2012 | McCafferty |
| 2012/0215838 | A1 | 8/2012 | Dominick et al. |
| 2012/0221310 | A1* | 8/2012 | Sarrafzadeh ......... A61B 5/0205 703/11 |
| 2013/0080425 | A1* | 3/2013 | Kwete ................ G06F 19/322 707/723 |
| 2013/0163838 | A1* | 6/2013 | Barr .................. G06F 19/321 382/131 |
| 2013/0238363 | A1* | 9/2013 | Ohta .................. G06Q 10/103 705/3 |
| 2013/0254703 | A1* | 9/2013 | Arling ................ G06F 19/345 715/781 |

FOREIGN PATENT DOCUMENTS

| | | |
|---|---|---|
| WO | 2004034903 A1 | 4/2004 |
| WO | 2013001439 A2 | 1/2013 |

OTHER PUBLICATIONS

Beymer et al., "Automatic Estimation of Left Ventricular Dysfunction from Echocardiogram Videos", IEEE Computer Society Conferrence on Computer Vision and Pattern Recognition Workshops, 2009, Jun. 20-25, 2009, pp. 164-171, © 2009 IEEE.
Beymer et al., "Cardiac Disease Recognition in Echocardiograms Using Spatio-temporal Statistical Models", 30th Annual International IEEE EMBS Conference, Vancouver, British Columbia, Canada, Aug. 20-24, 2008, pp. 4784-4788, © 2008 IEEE.
Blum et al., "Workflow mining for visualization and analysis of surgeries", Int J CARS, Received: Jan. 10, 2008, Accepted Jun. 3, 2008, © CARS 2008, DOI 10.1007/s11548-008-0239-0, Springer.
Bonow et al., Guidelines for the Management of Patients With Valvular Heart Disease: Executive Summary A Report of the American College of Cardiology/American Heart Association Task Force on Practice Guidelines (Committee on Management of Patients With Valvular Heart Disease), Circulation, Journal of the American Heart Assoc., Circulation, 1998;98:1949-1984, doi: 10.1161/01.CIR. 98.18.1949, Circulation is published by the American Heart Association, 7272 Greenville Avenue, Dallas, TX 75231, Copyright © 1998 American Heart Association, Inc.
Cheitlin et al., ACC/AHA/ASE 2003 Guideline Update for the Clinical Application of Echocardiography: Summary Article A Report of the American College of Cardiology/American Heart Association Task Force on Practice Guidelines (ACC/AHA/ASE Committee to Update the 1997 Guidelines for the Clinical Application of Echocardiography), JACC vol. 42, No. 5, 2003, Sep. 3, 2003:954-70, doi:10.1016/S0735-1097(03)01065-9, ©2003 by the American College of Cardiology Foundation and the American Heart Association, Inc.
Cortes et al., "Support-Vector Networks", Machine Learning, 20, pp. 273-297 (1995), © 1995 Kluwer Academic Publishers, Boston, Manufactured in The Netherlands.

Ebadollahi et al., "Echocardiogram Video Summarization", Medical Imaging 2001: Ultrasonic Imaging and Signal Processing, Michael F. Insana, K. Kirk Shung, Editors, Proceedings of SPIE vol. 4325 (2001) © 2001 SPIE, pp. 492-501.
Ebadollahi et al., "Echocardiogram Videos: Summarization, Temporal Segmentation and Browsing", © 2002 IEEE, IEEE ICIP 2002, pp. I-613-I-616.
Ferrucci et al., "UIMA: An Architectural Approach to Unstructured Information Processing in the Corporate Research Environment", To appear in a special issue of the Journal of Natural Language Engineering 2004, pp. 1-26.
Hirschberg et al., "Algorithms for the Longest Common Subsequence Problem", Journal of the Association for Computing Machinery, vol. 24, No. 4, Oct. 1977, pp. 664-675.
IHE Cardiology Technical Committee, "3D/4D Echocardiography Workflow", Integrating the Healthcare Enterprise, IHE Cardiology (CARD) White Paper, Aug. 5, 2011, Copyright © 2011: IHE International, Inc.
Jafari et al., "Enforcing Purpose of Use via Workflows", WPES'09, Nov. 9, 2009, Chicago, Illinois, USA.
Kühl et al., "High-Resolution Transthoracic Real-Time Three-Dimensional Echocardiography", Journal of the American College of Cardiology vol. 43, No. 11, 2004, © 2004 by the American College of Cardiology Foundation, Published by Elsevier Inc., doi:10.1016/j.jacc.2004.01.037, accepted Jan. 12, 2004, pp. 2083-2090.
Kumar et al., "Cardiac Disease Detection from Echocardiogram using Edge Filtered Scale-invariant Motion Features", Conference on Computer Vision and Pattern Recognition Workshops (CVPRW), 2010 IEEE Computer Society, Jun. 13-18, 2010, pp. 162-169, ©2010 IEEE.
Kumar et al., "Echocardiogram View Classification using Edge Filtered Scale-invariant Motion Features", IEEE Conference on Computer Vision and Pattern Recognition, 2009, CVPR 2009, Jun. 20-25, 2009, Miami, FL, pp. 723-730, © 2009 IEEE.
Kung, Sang Hwan, "Model and Performance of Real-time Workflow", SoftTech 2013, ASTL vol. 19, pp. 131-134, 2013.
Lang et al., "Results from Data Mining in a Radiology Department: The Relevance of Data Quality", Studies in Health Technology and Informatics, vol. 129: MEDINFO 2007, IOS Press, 2007, pp. 576-580.
Qian et al., "The Synergy of 3D SIFT and Sparse Codes for Classification of Viewpoints from Echocardiogram Videos", H. Greenspan et al. (Eds.): MCBR-CDS 2012, LNCS 7723, pp. 68-79, 2013, © Springer-Verlag Berlin Heidelberg 2013.
Reiner, Bruce, "New Strategies for Medical Data Mining, Part 3: Automated Workflow Analysis and Optimization", pp. 132-138, Copyright © 2011 American College of Radiology, DOI 10.1016/j.jacr.2010.07.004.
Silva et al., "Probabilistic Workflow Mining", KDD'05, Aug. 21-24, 2005, Chicago, Illinois, USA, Copyright 2005, ACM 1-59593-135-X/05/0008.
Singh et al., "The Origin of Echocardiography", A Tribute to Inge Edler, Texas Heart Institute Journal, vol. 34, No. 4, 2007, pp. 431-438, © 2007 by the Texas Heart® Institute, Houston.
Sun et al., "Incremental Workflow Mining with Optional Patterns and Its Application to Production Printing Process", International Journal of Intelligent Control and Systems, vol. 12, No. 1, Mar. 2007, pp. 45-55.
Van Der Aalst et al., "Workflow mining: A survey of issues and approaches", Data & Knowledge Engineering 47, (2003), pp. 237-267, accepted Feb. 26, 2003, © 2003 Elsevier B.V., doi:10.1016/S0169-023X(03)00066-1.
Zhou et al., "Image-based multiclass boosting and echocardiographic view classification", Proceedings of the 2006 IEEE Computer Society Conference on Computer Vision and Pattern Recognition (CVPR'06), 0-7695-2597-0/06, © 2006 IEEE.
Zoghbi et al, "Guidelines American Society of Echocardiography: Recommendations for Evaluation of the Severity of Native Valvular Regurgitation with Two-dimensional and Doppler Echocardiography", accepted Jul. 24, 2003, © 2003 The American Society of Echocardiography. Published by Elsevier Ltd.

(56) References Cited

OTHER PUBLICATIONS

U.S. Appl. No. 61/905,189, entitled "Prediction of Diseases Based on Analysis of Medical Exam and/or Test Workflow", filed Nov. 16, 2013.
Wayback Machine, ASE Guideline Documents by Publication Date—American Society of Echocardiography, Dec. 16, 2012, <https://web.archive.org/web/20121216082715/http://www.asecho.org/i4a/pages/index.cfm?pageID=4475>.

* cited by examiner

| | SUBFLOW DICTIONARY | | | LONGEST COMMON SUBFLOW | | |
|---|---|---|---|---|---|---|
| | CONTROL | DISEASED | MEAN | CONTROL | DISEASED | MEAN |
| TRICUSPID REGURGITATION | 66 % | 74 % | 70.0 % | 59 % | 61 % | 60.0 % |
| MITRAL REGURGITATION | 65 % | 74 % | 69.5 % | 56 % | 57 % | 56.5 % |
| LV HYPERTROPHY | 61 % | 74 % | 67.5 % | 56 % | 58 % | 57.0 % |
| AORTIC SCLEROSIS | 62 % | 71 % | 66.5 % | 54 % | 52 % | 53.0 % |
| AORTIC REGURGITATION | 66 % | 74 % | 70.0 % | 56 % | 50 % | 53.0 % |
| ATRIAL FIBRILLATION | 67 % | 78 % | 74.0 % | 53 % | 53 % | 53.0 % |
| LEVOCARDIA | 95 % | 94 % | 95.5 % | 70 % | 71 % | 70.5 % |
| OVERALL | 68.9 % | 77.0 % | 72.9 % | 57.7 % | 57.4 % | 57.6 % |

…

PREDICTION OF DISEASES BASED ON ANALYSIS OF MEDICAL EXAM AND/OR TEST WORKFLOW

BACKGROUND OF THE INVENTION

The present invention relates generally to the field of data mining, and more particularly to mining medical data.

A workflow consists of a sequence of connected steps. In some workflows: (i) the steps are performed in a series order (no overlapping steps); and (ii) there is no delay or gap between consecutive steps. Other workflows are more complicated. Workflow is a depiction of a sequence of operations, declared as work of a person or group, an organization of staff, or one or more simple or complex mechanisms. Workflow may be seen as any abstraction of real work that is actually performed in the real world. For control purposes, workflow may be a view of real work in a chosen aspect, thus serving as a virtual representation of actual work. Workflows may be viewed as one fundamental building block to be combined with other parts of an organization's structure such as information silos, teams, projects, policies and hierarchies. In medical imaging, modalities are defined as any of the various types of equipment or probes used to acquire images of the body. Modalities typically do not refer to the equipment but the nature of data that is obtained from it. For example, it is possible for magnetic resonance imaging (MRI) equipment to generate multiple modalities of data. In the case of medical imaging, modalities respectively correspond to various types of diagnostic images. More specifically, in case of echocardiogram images, there are multiple types of modalities that are generated by the same physical equipment as will be further identified, below.

Disease prediction is currently done by carrying out detailed analysis of various medical exams and tests. These exams and tests are computationally expensive, time consuming, and may not account for the exam in a holistic manner.

Sixty years since its invention, echocardiography remains a critical tool in the hands of cardiologists for the diagnosis and treatment of a multitude of cardiac diseases. Echocardiography is widely used for reasons including the following: (i) relatively noninvasive nature; (ii) ease of use; (iii) associated low costs; (iv) the array of useful clinical information about the heart structure; and (v) provides blood flow and motion information.

Echocardiography examines the heart with ultrasound waves. Using the core technology of capturing reflected ultrasound, detailed 2D (two dimensional) or 3D (three dimensional) images of the heart, as well as the characterization of blood flow (Doppler), are being constructed. In the course of an exam, an expert sonographer typically: (i) switches among various modalities (3D Video, 2D Video, M-mode (time-motion mode), CW (continuous wave)-Doppler, PW (pulse wave)-Doppler and their hybrids); (ii) systematically examines the heart walls, valves and blood flow from various viewpoints; and (iii) makes and records critical measurements.

The American College of Cardiology, the American Heart Association, and the American Society of Echocardiography, among others, have provided detailed guidelines and protocols in this regard. In addition to the prior knowledge about the patient and these guidelines, findings during the course of an exam also guide a sonographer as he decides on what modality to look at next. Typical modalities encountered in an echocardiogram are: (i) 2D Video (used to study heart structure); (ii) CW Doppler (used to study blood flow through the heart valves); (iii) PW Doppler (used to study blood flow in a localized region); (iv) Color Doppler (used to study blood flow in the context of the heart structure); (v) M Mode (used to study local structure movements over time); and (vi) Text (used to record or lookup measurements).

A radiologist or cardiologist typically examines the echocardiogram, as constructed by the sonographer, for the final diagnosis. This examination can be arduous and expensive. A typical echocardiogram can generate up to 3000 image frames and text. Some automatic intelligent summarization of such exams has been attempted, but these do not provide any diagnostic insight to the doctors. Conventional workflow analysis is largely focused on identifying deviation from a standard workflow or discovering a workflow from a collection of noisy and incomplete activity logs. In the medical field, given the high costs and complexity, there has been an increased focus in the policy sphere to standardize workflow and automatically record workflow operations for applications like auditing. There have also been some attempts to automatically analyze workflows to standardize processes like surgeries, and use them for teaching. Automatic mining of workflows, from radiology departments in particular, has been used to assess recorded data quality and deviations from standard workflows.

SUMMARY

According to an aspect of the present invention, there is a method, computer program product and/or system which performs the following actions (not necessarily in the following order): (i) receiving a first medical workflow obtained from a plurality of medical acts performed in sequence that related to care of a patient; and (ii) applying a set of condition-indication rules to the first medical workflow to determine first condition information which relates to a likelihood that a first medical condition exists in the patient. The receiving and applying steps are both performed by a machine that is controlled by machine logic.

DETAILED DESCRIPTION

Figure 1:
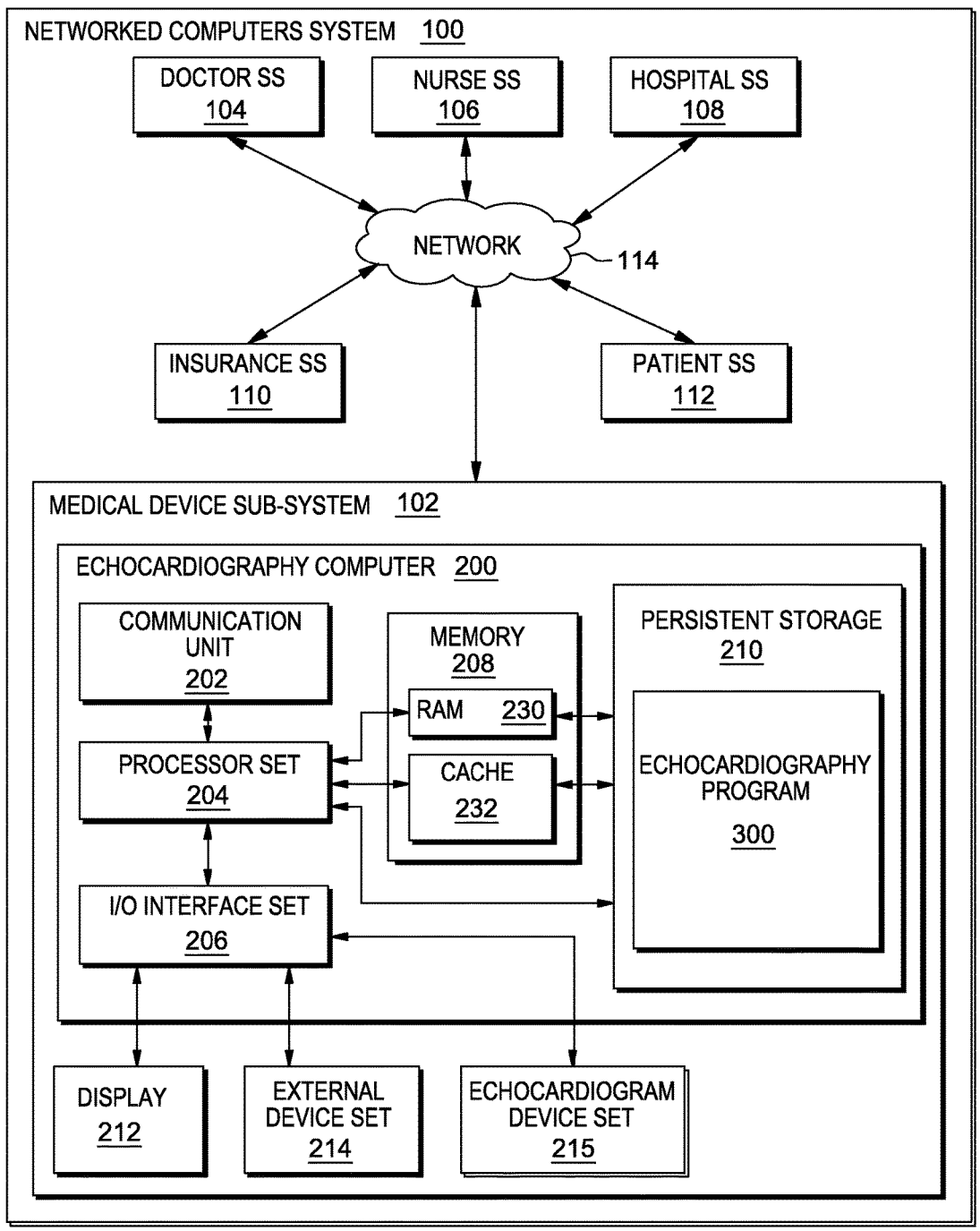
FIG. 1 is a schematic view of a first embodiment of a networked computers system according to the present invention.

This Detailed Description section is divided into the following sub-sections: (i) The Hardware and Software Environment; (ii) First Embodiment; (iii) Further Comments and/or Embodiments; and (iv) Definitions.

I. The Hardware and Software Environment

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer-readable medium(s) having computer readable program code/instructions embodied thereon.

Any combination of computer-readable media may be utilized. Computer-readable media may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Program code embodied on a computer-readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as JAVA (note: the term(s) "Java" may be subject to trademark rights in various jurisdictions throughout the world and are used here only in reference to the products or services properly denominated by the marks to the extent that such trademark rights may exist), Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

An embodiment of a possible hardware and software environment for software and/or methods according to the present invention will now be described in detail with reference to the Figures. FIG. 1 is a functional block diagram illustrating various portions of networked computers system 100, including: medical device sub-system 102; doctor sub-system 104; nurse sub-system 106; hospital sub-system 108; insurance sub-system 110; patient sub-system 112; and communication network 114. Medical device sub-system 102 includes: echocardiography computer 200; communication unit 202; processor set 204; input/output (i/o) interface set 206; memory device 208; persistent storage device 210; display device 212; external device set 214; echocardiogram device set 215; random access memory (RAM) devices 230; cache memory device 232; and program 300. Medical device sub-system 102 is generally similar to any sub-system made up largely of a general purpose computer with two exceptions: (i) the presence of echocardiography program 300 (this component will be discussed in detail in the following sub-section); and (ii) attachably detachable echocardiogram device set 215 for performing echocardiograms on human patients for diagnostic purposes. Echocardiogram device set 215 may be any echocardiogram device set now known or to be developed in the future, and it communicates medical images, and/or data needed to construct medical images, to echocardiography computer 200.

Computer 200 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a is a collection of machine readable instructions and/or data that is used to create, manage and control certain software functions that will be discussed in detail, below, in the First Embodiment sub-section of this Detailed Description section.

Sub-system 102 is capable of communicating with other computer sub-systems via network 114 (see FIG. 1). Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

FIG. 1 provides only an illustration of one implementation (that is, system 100) and does not imply any limitations with regard to the environments in which different embodiments may be implemented. Many modifications to the depicted environment may be made, especially with respect to current and anticipated future advances in cloud computing, distributed computing, smaller computing devices, network communications and the like.

Sub-system 102 is shown as a block diagram with many double arrows. These double arrows (no separate reference numerals) represent a communications fabric, which provides communications between various components of sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply some, or all memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the device on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102, such as sub-systems 104, 106, 108, 110, and 112 of other parties who may be interested in, and authorized to receive, medical data. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

II. First Embodiment

Preliminary note: The flowchart and block diagrams in the following Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 2:
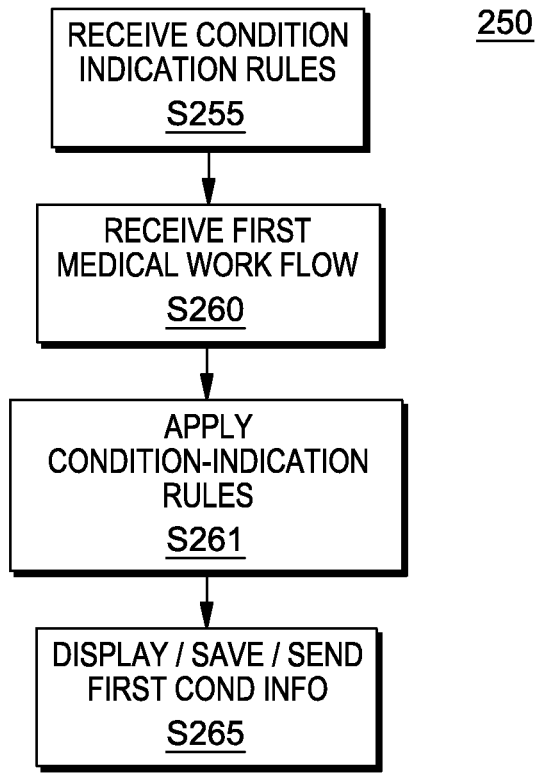
FIG. 2 is a flowchart showing a process performed, at least in part, by the first embodiment computer system.
Figure 3:
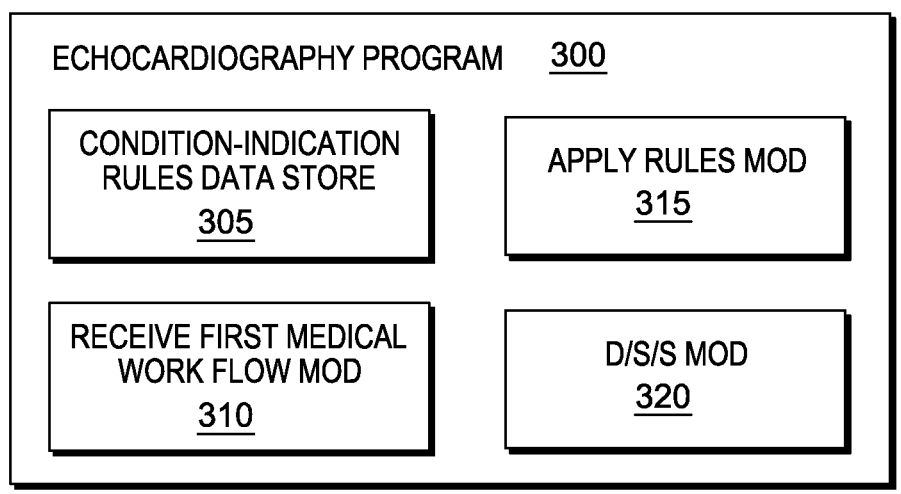
FIG. 3 is a schematic view of a echocardiogram program portion of the first embodiment computer system.

FIG. 2 shows a flow chart 250 depicting a method according to the present invention. FIG. 3 shows program 300 for performing at least some of the method steps of flow chart 300. This method and associated software will now be discussed, over the course of the following paragraphs, with extensive reference to FIG. 2 (for the method step blocks) and FIG. 3 (for the software blocks).

Processing begins at step S255, where echocardiography program 300 receives multiple condition-indication rules and stores them in condition-indication rules data store 305. These rules may be obtained by: (i) human experts; (ii) machine learning; or (iii) a combination of the foregoing ways. In this example, the condition-indication rules are limited in scope to rules regarding detection of heart-related conditions that are detectable by echocardiography. Alternatively or additionally, other embodiments may deal with other heart condition detection techniques and/or non-heart-related medical conditions.

In this embodiment, each rule includes: (i) a qualifying workflow (or set of workflows); and (ii) a consequential portion. A simple example of a set of condition-indication rules would be a "codebook" where each rule is: (i) a single qualifying workflow; and (ii) a consequential portion in the form of a condition (including, as appropriate, the "healthy condition") that is most likely to be associated with the qualifying workflow.

However, this embodiment further includes some rules which are different in form, such as: (i) rules that apply to all uses (such as a minimum similarity threshold before an input workflow can be considered as similar to any of the qualifying workflows); (ii) rules for conditionally determining that standards under which similarity is adjudged (for example, length input workflows may require less similarity to a qualifying workflow than a shorter input workflow would); (iii) negative rules for ruling out likely conditions based on dissimilarity; (iv) rules that marginally, add to or subtract from, likelihoods of one or more condition(s), rather than simply identifying a single condition as likely, such that similarity/dissimilarity of an input workflow vis-à-vis the qualifying workflows associated with several qualifying workflows is used to generate an ultimate condition information statement; and/or (v) rules that make adjustments for a version of the guidelines under which a given echocardiography workflow was performed.

Processing proceeds to step S260, where receive first medical workflow module ("mod") 310 receives a first input workflow (herein referred to as a "medical workflow"). A medical workflow is a workflow used in an actual examination of a real patient, unlike the qualifying workflows associated with the condition-indication rules. In this embodiment, the medical workflow is limited to a sequence of modalities used, by a human sonographer, in creating a set of echocardiogram data. These echocardiogram modalities will be discussed in more detail in the following sub-section. In other embodiments, the medical workflows may be constituted by, or at least include, a sequence of echocardiogram modalities examined by a doctor who reviews echocardiogram medical image data sets. In still other embodiments, the sequential events of the medical workflow may involve other types and/or modalities of medical imaging, and may not even involve medical imaging at all.

However, as one considers the possibilities here, it should be kept in mind that a medical workflow will generally be limited to the fact that certain medical acts were performed in a certain sequence, and will not contain substantive information discovered in the course of performing the medical acts. For example, if the medical acts all involve medical imaging, then the workflow would not include the images themselves, which would be traditional medical diagnosis techniques. The present invention does not seek to cover traditional medical diagnosis techniques (but, rather, only to cover certain supplementations of these techniques).

Processing proceeds to step S261, where apply rules mod 315 applies any, and all, applicable condition-indication rules in order to yield a condition information statement. The condition information statement includes, at least, information related to the likelihood of the patient (who was the subject of the medical workflow) having at least one condition. Some example of medical conditions that can be detected (or at least probabilistically detected) by echocardiography will be discussed in the next sub-section of this document.

In some embodiments, the condition information statement may simply say: "the most likely diagnosis is that the patient has condition x." Other types of condition information statements may give relative probabilities of the likelihood of multiple different conditions existing.

In a typical case, a condition-indication rule is applied to the medical workflow by comparing the medical workflow to the qualifying workflow associated with the rule. In some, if not all embodiments, the requisite similarity/dissimilarity between an actual workflow and the qualifying workflow of a given rule required to invoke the given rule is reducible to an algorithm that can be programmed into machine logic (hardware and/or software). The next sub-section of this document will discuss at least one possible "similarity algorithm." Mod 315 determines that the medical algorithm is sufficiently similar (or dissimilar, depending upon how the rule is written) to the qualifying algorithm; then the consequential portion of the rule is invoked. In some cases, the consequential portion of the rule will simply be informational (for example, "it is highly likely that the patient has condition X"). In another example, the rule may have a process component (for example, "the results are inconclusive and all other rules should be ignored" along with an instruction to cease application of other rules that would otherwise be applied). In yet another example, an informational component of the consequence portion of multiple rules are aggregated to build the condition information statement.

Processing proceeds to step S265 where display/save/send mod 320 displays (to display device 212 as shown in FIG. 1), saves (to persistent storage 210 as shown in FIG. 1) and sends (to the doctor, nurse, patient, hospital and insurance company sub-systems as shown in FIG. 1) the condition information statement generated at step S261.

III. Further Comments and/or Embodiments

Some embodiments of the present disclosure recognize that the workflow of an exam is powerful information that is ignored by conventional systems. Some embodiments of the present disclosure may include one or more of the following features, characteristics, and/or advantages: (i) a way of mining, in a totally data driven fashion, medical workflows to obtain disease information; (ii) use of a medical workflow to provide insights (in some embodiments, these insights are complementary to what is achieved by analyzing the actual content of the exams); (iii) quickly predict the likelihood of a disease by analyzing only the workflow patterns of a medical exam; (iv) does not look into the actual content of any medical exam; (v) provide medical practitioners a quick diagnostic insight into echocardiograms by only analyzing the echocardiogram workflows (defined as the sequence of modalities examined); (vi) define a dictionary of workflows called subflows; (vii) predict occurrences of diseases for any, yet unseen, echocardiogram workflow; (viii) creation of a "dictionary" of subflows by using a corpus of echocardiograms; (ix) identify ground truth diagnoses using expert created associated reports; (x) build discriminative models for multiple different cardiac diseases; (xi) predict diseases with an average of 75% accuracy using workflow input; and/or (xii) predict diseases by mining a collection of echocardiography workflow.

With respect to item (vi) of the previous paragraph, the subflows of the dictionary are commonly encountered in echocardiography workflows, and are mutually exclusive (at least in some embodiments). Each workflow is represented as a combination of dictionary subflows. In some embodiments, discriminative models for various cardiac diseases are attained by inputting the combination of subflows to a computer software based analytics system herein called a Support Vector Machine (SVM). SVM is just one embodiment of various possible computer software based analytics systems which may be used in conjunction with various embodiments of the present invention.

Some embodiments of the present invention recognize that given a large enough collection of echocardiogram workflows, patterns indicative of various diseases can be indentified (or at least established as being more or less likely). Some definitions: (i) workflow is any list made up of a time-ordered sequence of work related tasks (whether performed by people and/or machines) that have been performed; (ii) medical workflow is any medically-related workflow; (iii) cardio workflow is any workflow related to medical work substantially involving the heart; (iv) cardio-modality workflow is any cardio workflow where the sequence of work-related tasks is substantially made up of creating and/or examining different modalities; and (v) echocardiogram-modality workflow is any cardio workflow where the sequence of work-related tasks is substantially made up of creating and/or examining different echocardiogram modalities. Note that under these definitions, cardio-modality workflow and echocardiogram-modality workflow both require more than a single modality in order for there to be a meaningful workflow that involves going from one modality to another. In some embodiments of the present disclosure, a completely data driven approach is taken, meaning that the system will not be "biased" to look for a specific rule based pattern.

In some embodiments, starting with a collection of workflows, a dictionary of subflows (defined as a sub-sequence of a workflow) is created. The pre-defined subflows are then used as a basis to represent larger workflows that are observed in medical practice (that is, actual exams and/or tests). In some embodiments, subflows, useful as building blocks, are defined based: (i) the frequency of occurrence of the subflow; and (ii) the mutual exclusiveness of various subflow candidates. These subflows can be thought of as a way to extract features from a workflow. In some embodiments, using the labels obtained from expert created reports, all the workflows are transformed into a "feature space." The Support Vector Machine (SVM) can then be used to discriminate between an actual disease versus a control case. Given a new unseen workflow, features can be extracted and the SVMs can be used to predict the presence or absence of various diseases.

Within this landscape of workflow and echocardiography literature, one embodiment of this disclosure presents a novel approach to predicting diagnostic information by mining the collection of echocardiogram workflows. Not only are novel hypothesis explored, but novel methods are also presented, such as a dictionary based workflow classification, which are used to accomplish a set of goals.

In some embodiments, the echocardiogram data corpus is composed of 2300 echocardiogram exams and their associated expert-created reports. The echocardiogram data provided is in the form of a collection of video frames. These frames belong to video segments, called runs. To determine the workflow, the modality that each run belongs to needs to be determined. In the absence of the associated DICOM (Digital Imaging and Communications in Medicine) headers, and given the large number of runs, an automatic method to assign a label to each run is needed. For example, a run may be composed solely of a single 2D Video frame.

Figure 4:
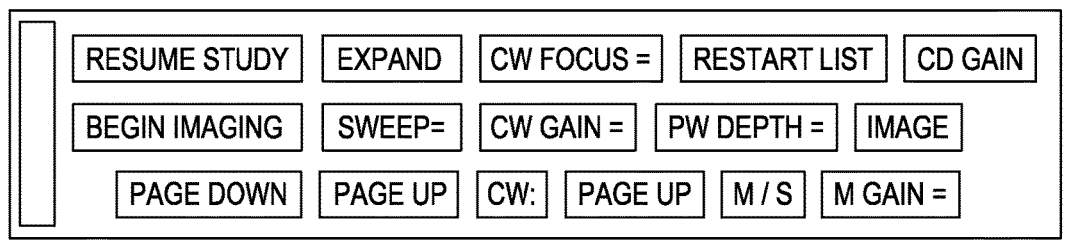
FIG. 4 is a screen shot showing a workflow diagram.

By manually analyzing the runs, certain characteristic image templates, for each modality, were determined. These templates are shown in diagram 400 of FIG. 4 and are used to indentify the modality a run belongs to. For each of these templates, the likely locations (that is, location within a display area) for the template's appearance, when working within that template's modality, was also determined. For each frame of the templates in diagram 400, a matching score is obtained using 2D cross-correlation. In some embodiments, image-identification rules are built using manual analysis with reference to a pre-existing corpus of medical displays (for example, echocardiogram displays). These image-identification rules serve to correlate new runs to various display modalities, with the above-describe templates being a factor in this rule-based run-to-modality correlation. In some echocardiogram embodiments, the modalities are as follows: (i) 2D, a run with a single 2d frame; (ii) 2DV, a 2D video run; (iii) text, a text display where image related information is presented to the user as text; (iv) PW, a PW Doppler run; (v) CW, a CW Doppler run; (vi) COLOR, a color Doppler run; (vii) MM, an M-Mode run; and (viii) UND, a run that defies easy classification such that this modality category serves as a "catch-all" for echocardiogram medical images that do not reliably fall into any of the previous categories. These eight echocardiogram modalities are shown in diagram 600 of FIG. 6 respectively as blocks: 622, 604, 626, 608, 610, 634, 630 and 614. Diagram 600 will be discussed in more detail later on in this sub-section.

Figure 5A:
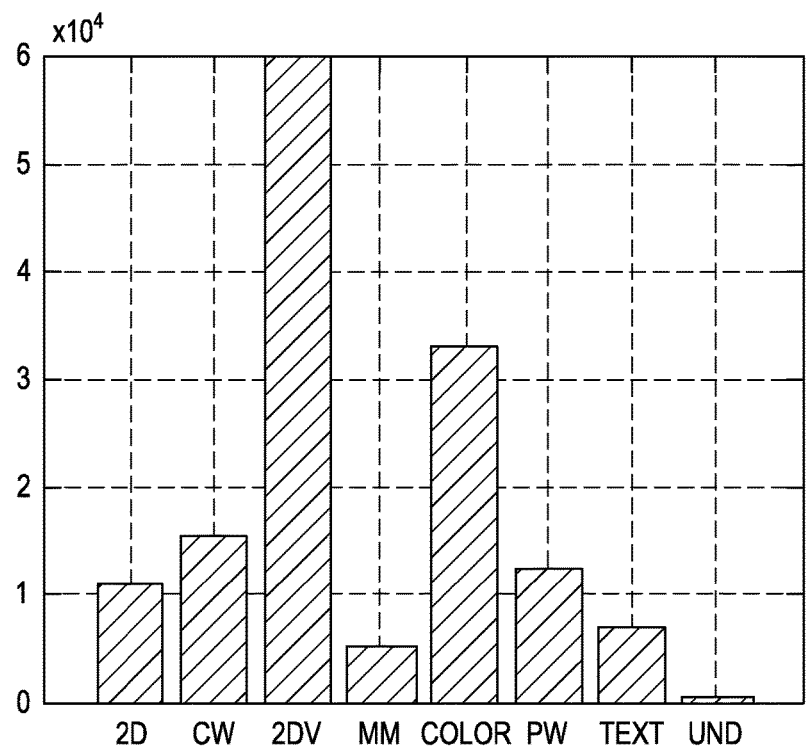
FIG. 5A is a bar charts showing the various modalities in the echocardiogram data corpus.

As shown in FIG. 5A, one example to illustrate rule making under some embodiments of the present invention involves a base corpus 143,786 runs. FIG. 5A shows bar chart 500a, which graphically illustrates how the runs of the base corpus can be divided into the various echocardiogram modalities identified above. In this example, 2D Video makes up over 40% of the runs, while the undefined cases make up less than 0.001% of the total runs.

In some embodiments, obtaining disease labels for echocardiograms also involves automatic processing by software. In some embodiments, this software-based processing is based on disease-identification rules. In these embodiments, the medical workflow is an input, which has disease-identification rules applied to it, to yield an output as to what the likeliest disease(s) are. It is noted that "disease" is used broadly in this document to refer to any physical condition, status or other phenomenon of medical interest.

Figure 5B:
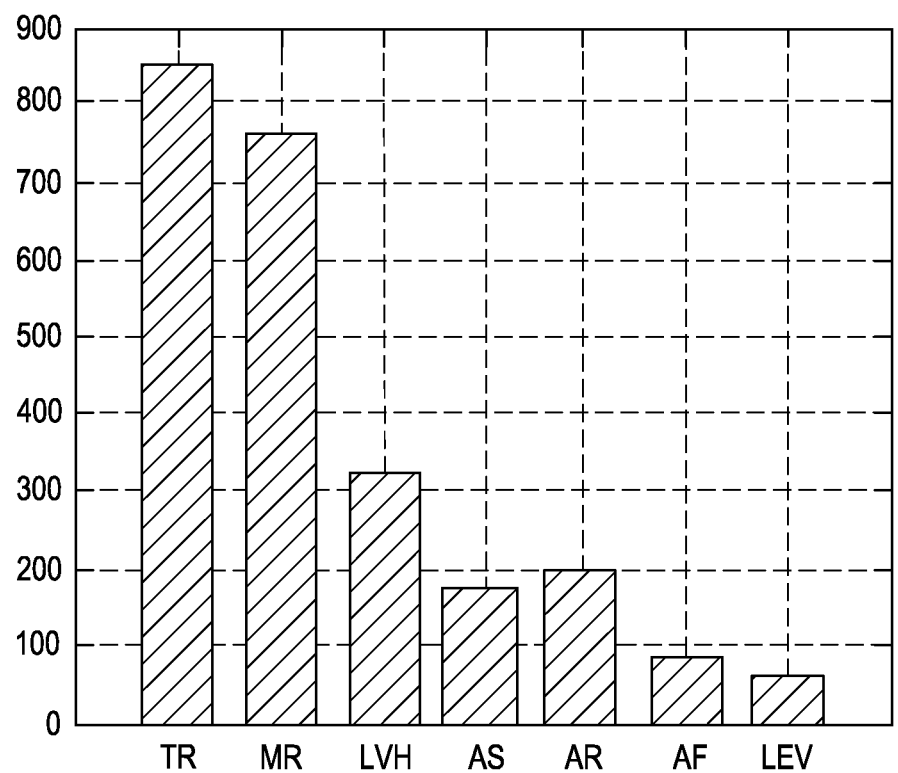
FIG. 5B is a bar chart showing the distribution of the diseases identified using expert created reports.

In this example, the reports in the base corpus of echocardiograms were created by experts but are composed of unstructured text in a natural language. Using a dictionary-based approach within the Apache UIMA (Unstructured Information Management Architecture), a list of diagnoses from each report was obtained. Bar chart 500b of FIG. 5B shows the distribution of the diseases that were automatically identified using these associated expert created reports. From the list of diseases, the seven (7) most frequent diseases were identified: (i) TR, Tricuspid Regurgitation; (ii)

MR, Mitral Regurgitation; (iii) LVM, Left Ventricular Hypertrophy; (iv) AS, Aortic Stenosis; (v) AR, Aortic Regurgitation; (vi) AF, Atrial Fibrillation; and (vii) Lev, Levocardia. The remaining echocardiograms (from the total of 2300 in the base corpus) were considered as control cases for each of the diseases noted. The dictionary-based approach ensured that there were very few, or no, false-positives in the diagnoses list.

Medical imaging workflow, and specifically echocardiogram workflow, will now be discussed. As previously mentioned, a sonographer, during the course of an exam, switches among various echocardiogram modalities as he explores the heart. The order of modalities used by the sonographer is guided by both: (i) pre-defined guidelines; and (ii) new information found as the exploration is performed. For example, guidelines for assessment of Aortic Stenosis dictate that CW Doppler be used to investigate jet velocity. This requires the use of 2D Video to position the beam over the aortic valve before CW Doppler modality imaging can be applied. Also, it is recommended that Color Doppler be used to avoid recording eccentric regurgitant jets from the mitral valve that may cause erroneous CW Doppler readings. To most sonographers, the above recommendation translates into using approximately similar sequences of modalities to investigate Aortic Stenosis. Furthermore, it is likely that in the event evidence of Aortic Stenosis is detected, the pattern used may be repeated by the sonographer to confirm the finding.

Echocardiography workflow is defined in this disclosure as a temporally ordered sequence of modalities that are examined in a given echocardiogram exam. As an example, a typical echocardiogram exam that was observed, is about 65 modalities long, while the maximum length observed is 211 modalities long. Note that echocardiogram guidelines sometimes define the workflow down to an even more granular level of specificity called viewpoint. Viewpoint refers to the combination of the position and the angle at which the ultrasound probe is placed on the patient. At times, the viewpoint data points associated with a run, is available in the DICOM header. Since the corpus in this example lacks DICOM headers, direct access to this information was not available. That said, there are automatic methods for determining the viewpoint in a given echocardiogram frame, of course, with associated inaccuracies, but for the sake of simplicity, workflow is simply defined in terms of the modalities explored.

An example of a typical echocardiogram workflow is: {2DV, 2DV, 2DV, 2DV, 2DV, Color, 2DV, Color, Color, 2DV, Color, CW, Color, CW, 2DV, 2DV, MM, 2D, 2DV, 2D, 2D, TEXT, Color, CW, Color, PW, CW, Color, PW, PW, MM, 2DV, 2D}. Each workflow will be donated by $w_1$ and the set of all workflows as $W=\{w_1, w_2, \ldots, w_{2300}\}$. As is evident, representing a workflow with an explicit listing of all the modalities can be cumbersome to read.

Figure 6:
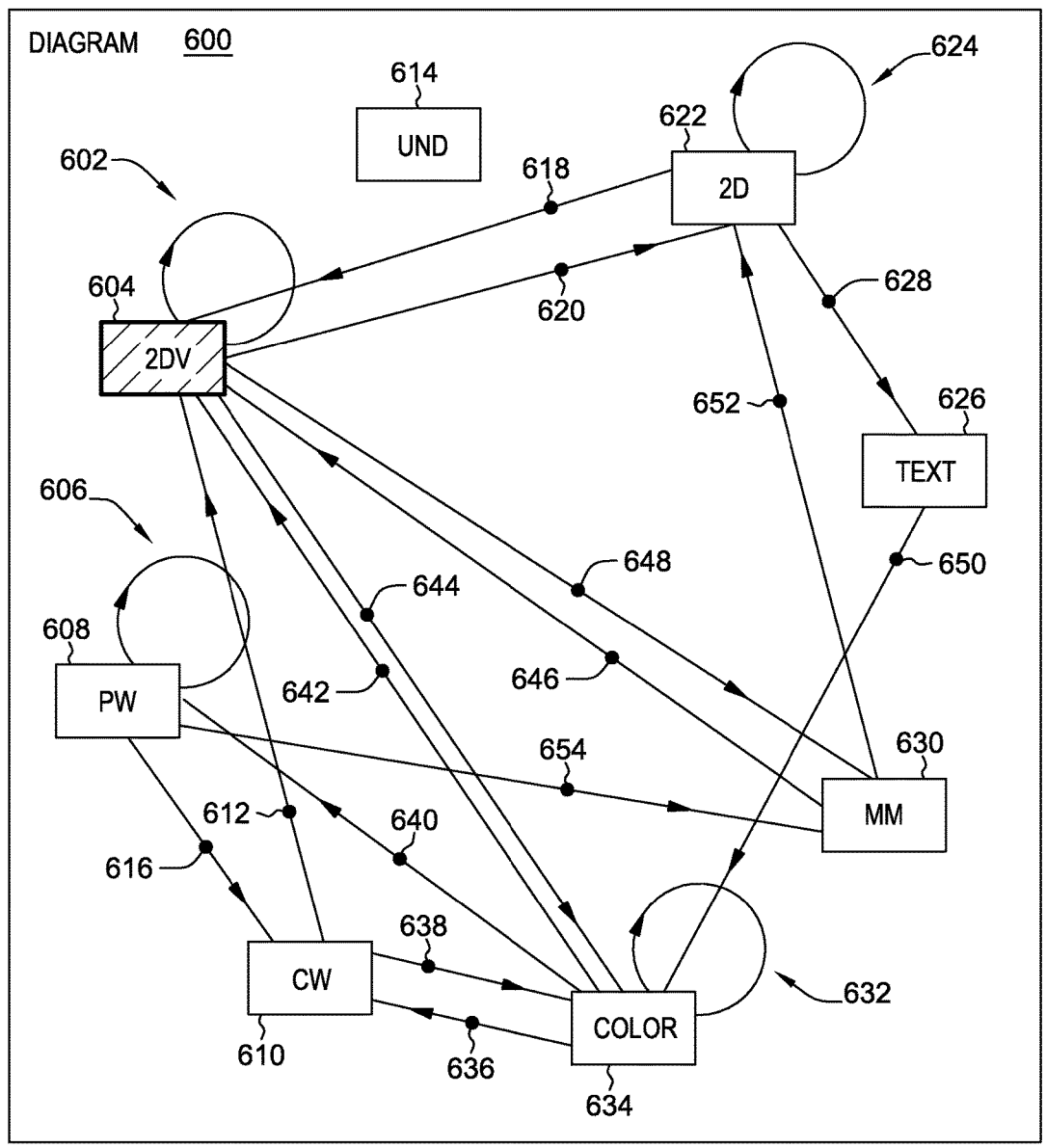
FIG. 6 is a state transition diagram for a workflow.

As shown in FIG. 6, state flow diagram 600 is presented for an example echocardiogram workflow. Diagram 600 represents the following workflow having a sequence of 33 modalities: {2DV, 2DV, 2DV, 2DV, 2DV, Color, 2DV, Color, Color, 2DV, Color, CW, Color, CW, 2DV, 2DV, MM, 2D, 2DV, 2D, 2D, TEXT, Color, CW, Color, PW, CW, Color, PW, PW, MM, 2DV, 2D}. In diagram 600, the rectangular boxes represent the different modalities. The arrows between the boxes (herein called "transition paths") represent a sequential progression by the sonographer from one modality to another (or, for the circular, looping arrows, another run in the same modality that was performed immediately previously). The start state is indicated by the cross-hatched rectangle 604. Although diagram 600 does not include any indication of the frequency that each transition path is followed by the sonographer during the echocardiogram, this can be indicated by color, line thickness, line pattern, or the like.

Diagram 600 also does not include any indication of which transition(s) in the workflow that a given arrow represents. However, diagrams can be annotated with this information, and such annotations, for the above workflow would read as follows: (i) arrow 602=1, 2, 3, 4, 15; (ii) arrow 606=29; (iii) arrow 612=14; (iv) arrow 616=26; (v) arrow 618=18; (vi) arrow 620=19, 32; (vii) arrow 624=20; (viii) arrow 628=21; (ix) arrow 632=8; (x) arrow 636=11, 13, 23; (xi) arrow 638=12, 24, 27; (xii) arrow 640=25, 28; (xiii) arrow 642=6, 9; (xiv) arrow 644=5, 7, 10; (xv) arrow 646=31; (xvi) arrow 648=16; (xvii) arrow 650=22; (xviii) arrow 652=17; and (xix) arrow 654=30.

In some embodiments of the present disclosure, automatically discovering patterns in data involves a definition of similarity, or distance, between any pair of entities. This allows a comparison between given entities and the ability to look for patterns that are common among similar and dissimilar entities. This problem is approached by first preparing a common basis for the representation of workflows. Without a common basis, comparing workflows is a challenge because they can be of differing lengths and composition.

An example of dictionary construction according to one embodiment of the present disclosure will now be discussed. To begin, a dictionary of salient subflows is defined. The dictionary elements are called subflows because of the way they are derived, and also due to the fact that they are typically smaller in length than a workflow. The objective is to assemble a set of subflows. These subflows will eventually be used to represent workflows, which are both descriptive and distinctive. The subflows are required to be descriptive, so that when used to represent other workflows, the representation is not too erroneous. The subflows are also required to be distinctive so that redundant information is not recorded in the basis dictionary.

Foremost, all the possible pairs of workflows were analyzed, and from this the longest common subsequences (LCS) were derived. Note that a LCS does not have to be contiguously present in the parent workflows. As an example, if $w_1=\{2DV, 2DV, Color, CW, PW, MM, 2DV, 2D\}$ and $w_2=\{Color, CW, Color, CW, 2DV, 2DV\}$, LCS ($w_1$, $w_2$)={Color, CW, 2DV}. In this example, the base corpus lead to over 4 million subflows being derived using this pair wise analysis.

In order to reduce the number of elements in this large set, only the 10,000 most frequently occurring subflows were retained in this example. This step should retain only the most descriptive subflows. Next, subflows that are less than 3 modalities long are removed. This is done so as to not admit subflows into the dictionary that will be found in almost all of the workflows. Finally, a pair wise analysis of the retained subflows is performed. If a set of subflows $\{s_1, s_2, \ldots, s_k\}$ is found such that $s_1 \in s_2 \in \ldots \in s_k$, where $s_i \in s_j$ represents LCS($s_i$, $s_j$)=$s_i$, only retain $s_k$ is retained. This is done because any information that is captured by $s_1$ through $s_{k-1}$ is present in $s_k$. Doing this further reduces the amount of redundancy in the dictionary. After these steps, a collection of only 172 subflows remain that are sufficiently descriptive and distinctive. The dictionary is represented where $D=\{e_1, e_2, \ldots e_{172}\}$, and where $e_i$ are the dictionary elements.

The top five (5) elements of the dictionary are presented in FIGS. 7A through 7E. Note that the top entry is simply a loop of two directional arrows running between 2D Video and Color Doppler modalities. Also apparent is the fact that the 2D Video modality forms an anchor point from which transition to most other modalities takes place. Transitions between CW Doppler and Color Doppler are also frequent, as one would expect going by the guidelines.

Figure 7A:
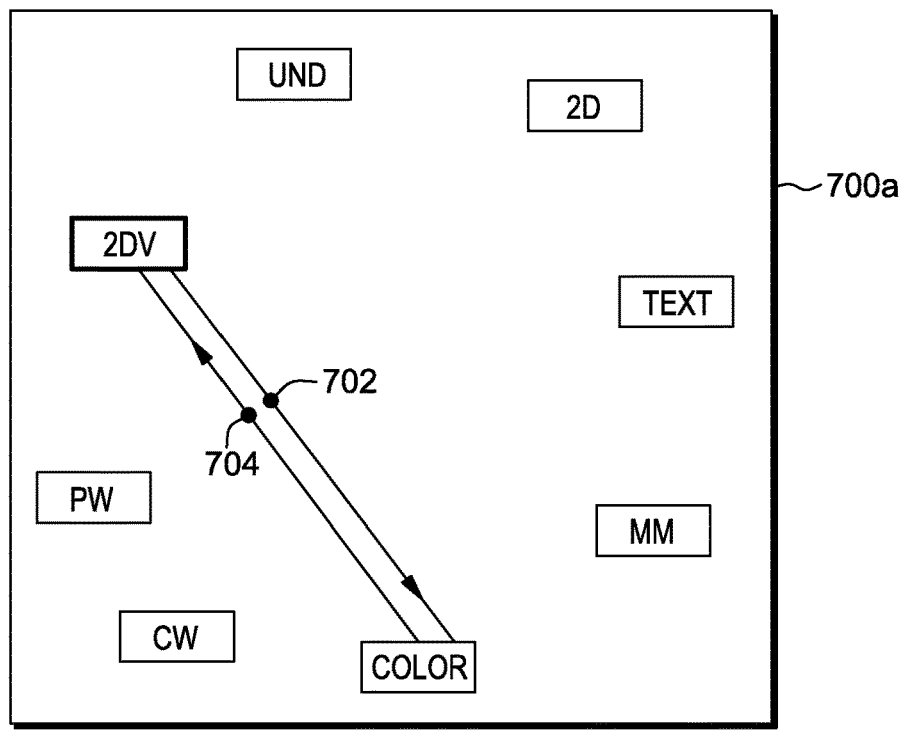
FIGS. 7A through 7E show the top five (5) elements of the subflow dictionary.

In diagram 700a of FIG. 7A, the following paths are respectively associated with the following transition numbers: (i) arrow 702=1, 3, 5, 7, 9, 11, 13, 15, 17, 19, 21, 23, 25, 27; and (ii) arrow 704=2, 4, 6, 8, 10, 12, 14, 16, 18, 20, 22, 24, 26, 28.

Figure 7B:
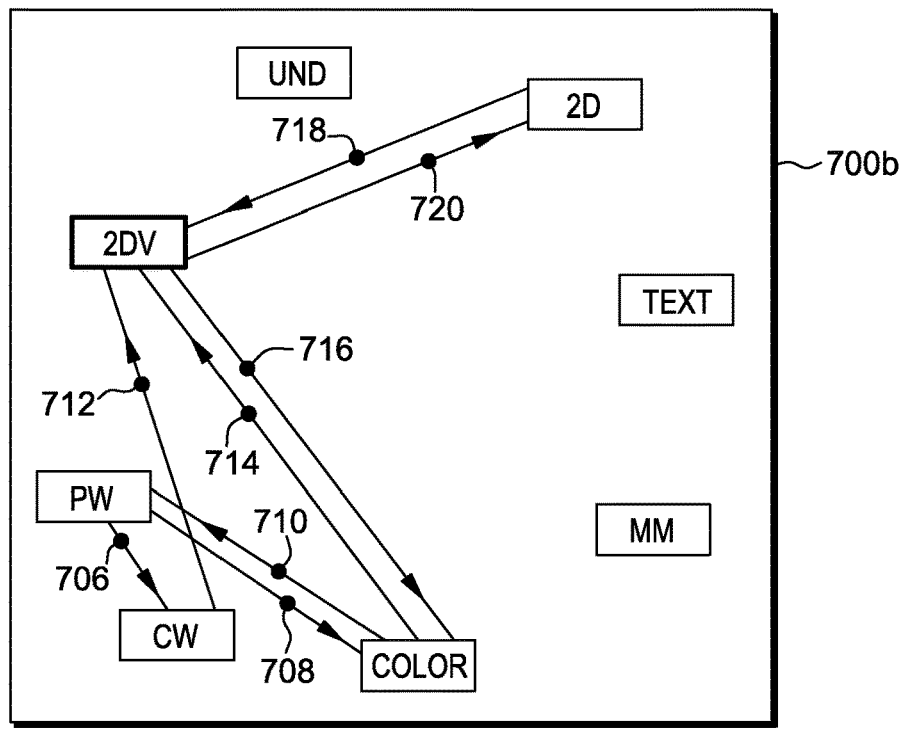

In diagram 700b of FIG. 7B, the following paths are respectively associated with the following transition numbers: (i) arrow 706=21; (ii) arrow 708=13; (iii) arrow 710=12, 20; (iv) arrow 712=22; (v) arrow 714=2, 6, 8, 10, 14, 16, 18, 24; (vi) arrow 716=1, 5, 7, 9, 11, 15, 17, 19, 23, 25; (vii) arrow 718=4; and (viii) arrow 720=3.

Figure 7C:
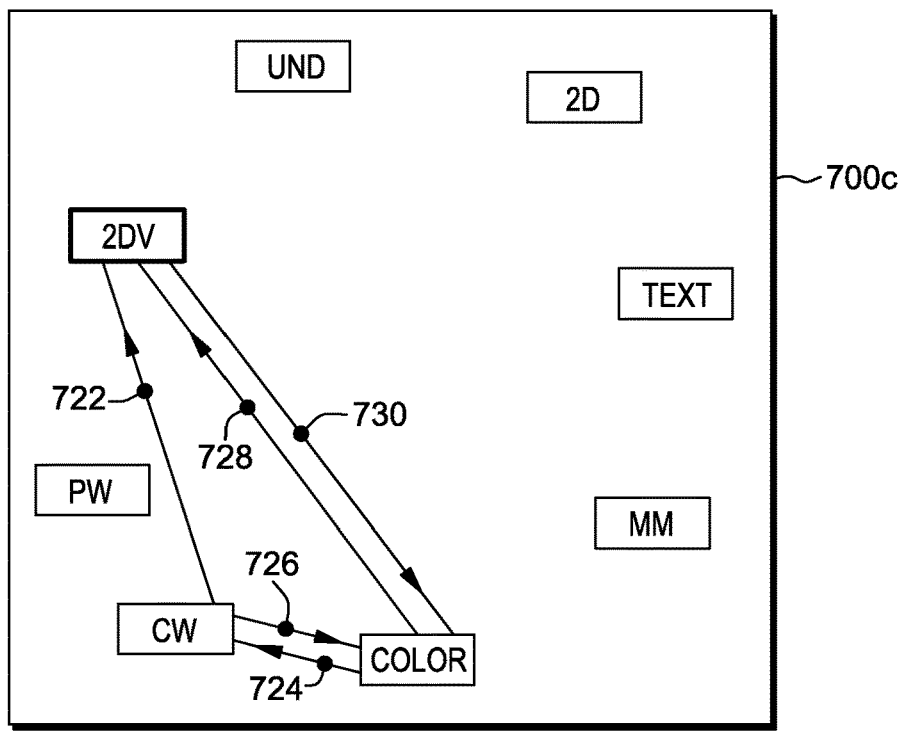

In diagram 700c of FIG. 7C, the following paths are respectively associated with the following transition numbers: (i) arrow 722=9, 14; (ii) arrow 724=6, 8, 13; (iii) arrow 726=7; (iv) arrow 728=2, 4, 11, 16, 18, 20, 22, 24; and (v) arrow 730=1, 3, 5, 10, 12, 15, 17, 19, 21, 23, 25.

Figure 7D:
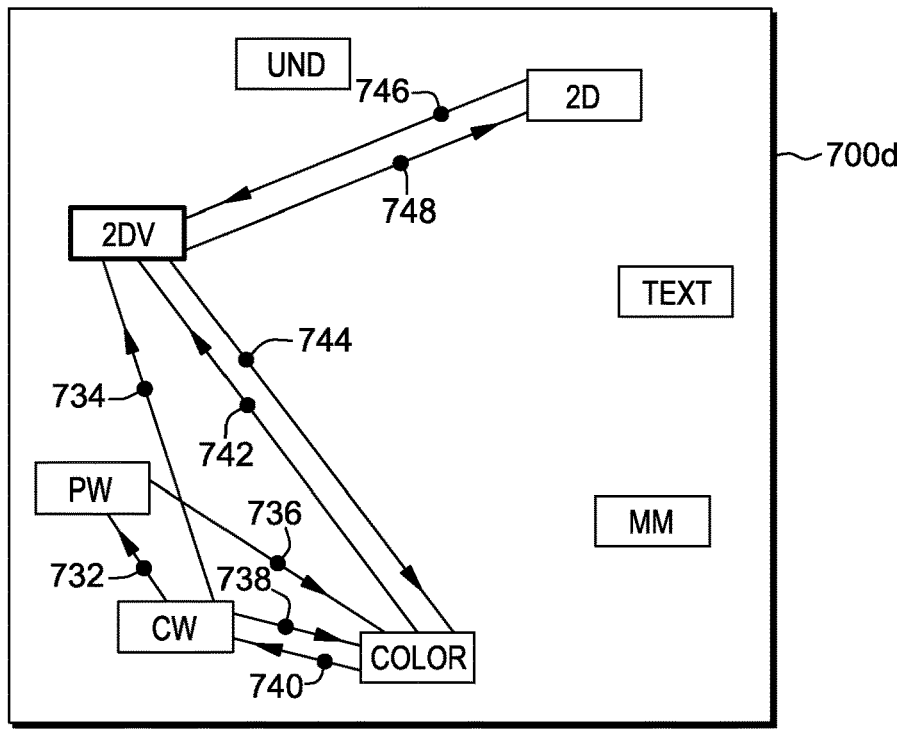

In diagram 700d of FIG. 7D, the following paths are respectively associated with the following transition numbers: (i) arrow 732=15; (ii) arrow 734=18; (iii) arrow 736=16; (iv) arrow 738=9, 13; (v) arrow 740=8, 12, 14, 17; (vi) arrow 742=4, 6, 10, 20, 22, 24; (vii) arrow 744=3, 5, 7, 11, 19, 21, 23, 25; (viii) arrow 746=2; and (ix) arrow 748=1.

Figure 7E:
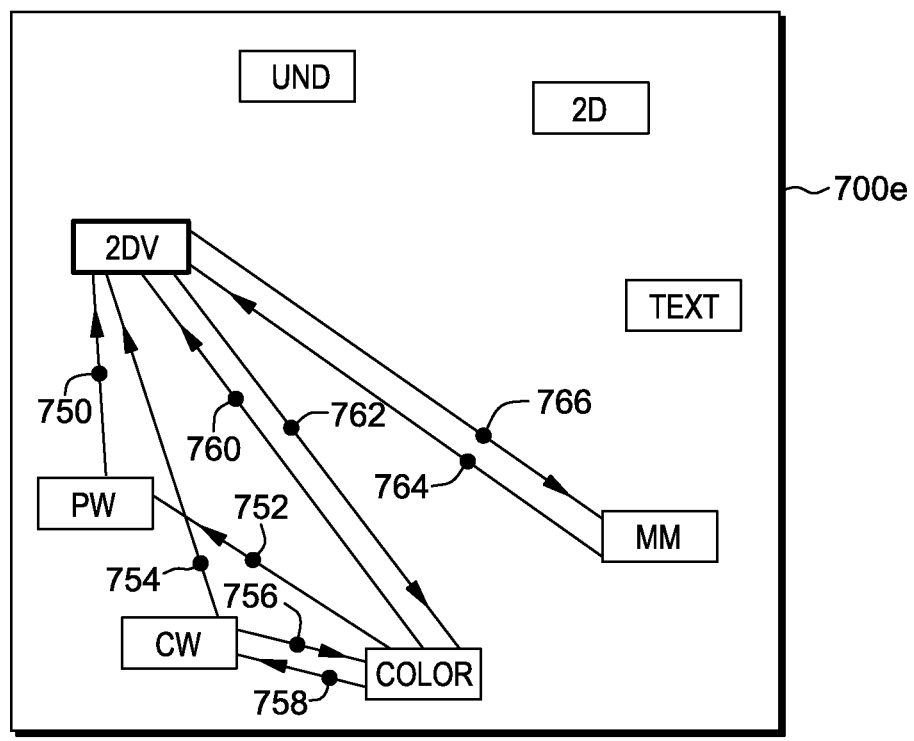

In diagram 700e of FIG. 7E, the following paths are respectively associated with the following transition numbers: (i) arrow 750=18; (ii) arrow 752=17; (iii) arrow 754=5, 10, 15, 23; (iv) arrow 756=8, 13; (v) arrow 758=4, 7, 9, 12, 14, 22; (vi) arrow 760=20, 25; (vii) arrow 762=3, 6, 11, 16, 19, 21, 24; (viii) arrow 764=2; and (ix) arrow 766=1.

Workflow Representation will now be discussed. Once the subflow dictionary has been created, a method to represent each workflow is defined in terms of dictionary elements, no matter its composition or length. This can be accomplished by comparing a given workflow $w_i$ against each of the dictionary elements and recording the length of the LCS matching score. This is defined as:

$$p_{ij} = \text{length}(\text{LCS}(w_i, e_j))/\min(\text{length}(w_i), \text{length}(e_j)).$$

Note that this translates each workflow ($w_i$) into a 172-dimensional vector ($p_i$), where each dimension shows the amount of overlap the workflow has with each of the dictionary elements. Once in the 172-dimensional subflow space, any of the various vector distances, for example cosine distance, Euclidian distance, and so on, can be used to compute distances between the workflows. Thus, the distance between two workflows $w_i$ and $w_j$ is defined as:

$$D_{Dictionary}(w_i, w_j) = d(p_i, p_j), \text{ where } d \text{ is any vector space distance.}$$

The Discriminative Disease Model will now be discussed. One embodiment of this disclosure is the novel representation of workflows, where the goal is to build models that can help identify possible diagnoses. To accomplish this, the SVM framework is called upon. An SVM is a classifier that, when used with two classes, tries to find a boundary in the data space such that the two classes are separated by the maximum possible margin. Given a set of training data, which is composed of a set of vectors and their labels, SVM tries to find the parameters of this maximum margin boundary. This boundary can be thought of as a high dimensional line, which is characterized by a set of weights ($\alpha$). Since the objective of this work is to predict occurrence of each of the seven (7) cardiac diseases previously identified (see FIGS. 5A and 5B), one SVM model is built for each of the diseases.

FIGS. 8A through 8G (respectively diagrams 800a to 800g) show the SVM model parameters for the seven (7) selected diseases. The absolute value along a dimension indicates the high importance of the associated dictionary subflow in the discriminative model. The seven (7) diseases are: (i) FIG. 8A=TR: Tricuspid Regurgitation; (ii) FIG. 8B=MR: Mitral Regurgitation; (iii) FIG. 8C=LVM: Left Ventricular Hypertrophy; (iv) FIG. 8D=AS: Aortic Stenosis; (v) FIG. 8E=AR: Aortic Regurgitation; (vi) FIG. 8F=AF: Atrial Fibrillation and; (vii) FIG. 8G=Lev: Levocardia.

Diagrams 800a, b, c, d, e, f and g, show the SVM parameters ($\alpha$) that were acquired for the seven (7) diseases noted above, where $\alpha$ is a 172-dimensional vector. A large absolute value along a dimension of $\alpha$ indicates the high importance of that particular dimension and associated dictionary element in the disease discriminative model. Note, if the three (3) most important dictionary elements (subflows) for each of the seven (7) diseases above are considered, there is a total of twenty one (21) subflows. Even within this small set, one (1) subflow for TR can be found to repeat four (4) times in these twenty one (21) noted subflows.

The results of this disclosure will now be discussed. For each disease and its associated control group, several blind experiments were conducted to test the workflow mining framework described above. In each experiment, 95% of the data was used to train the model and the remaining 5% to test. These experiments were repeated ten (10) times and the average accuracy number is reported in diagram 900 of FIG. 9. Also note the section of diagram 900 labeled "Subflow Dictionary." The numbers under the column "Control" represent the percentage of test workflows that were labeled by experts as disease free that were correctly classified within the scope of this disclosure. The numbers under the column "Diseased" show the same percentage for expert labeled diseased cases. The "Mean" column reports the average of the "Diseased" and "Control" columns.

In addition to experiments on the proposed method, a baseline method for comparison was also tested. These results are also presented in FIG. 9, in the section labeled "Longest Common Subflow". Instead of defining the distance between workflows via a dictionary, here a score based on overlap between two workflows is used. As per this definition, the distance between workflows $w_i$ and $w_j$ is given as:

$$D_{LCS}(w_i, w_j) = \text{length}(\text{LCS}(w_i, w_j))/\min(\text{length}(w_i), \text{length}(w_j)).$$

For the binary classification task, it can be noted that "Longest Common Subflow" does not perform much better than chance. Recall that even a random classifier should be able to attain 50% accuracy. In comparison, the proposed dictionary based method performs significantly better.

In this disclosure, the target is to quickly provide a summary of possible diseases in a given echocardiogram exam to the doctors so as to help them in their task of diagnosing the patient. In conjunction with a traditional video summarization system, this system contributes critical value add, where, on average, diseases can be predicted with 77% accuracy. For context, an automatic method for disease detection that works with 2D Video, and requires a substantial amount of image processing, attains an average of 80% accuracy.

Figure 8A:
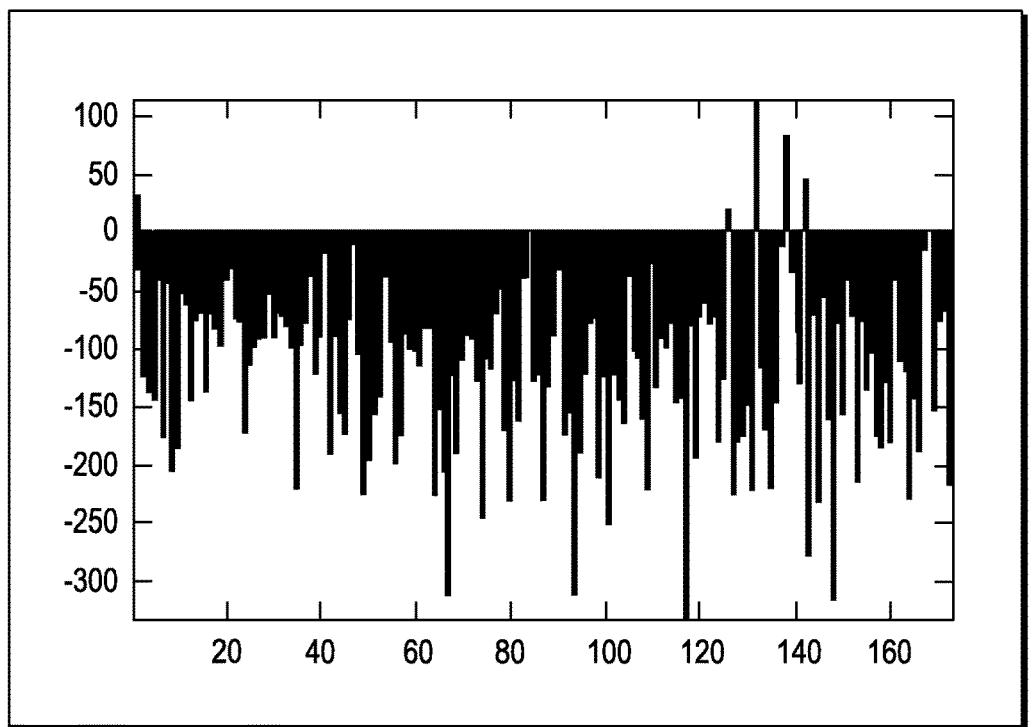
FIGS. 8A through 8G show the SVM (Support Vector Machines) model parameters for the seven (7) selected diseases.
Figure 8B:
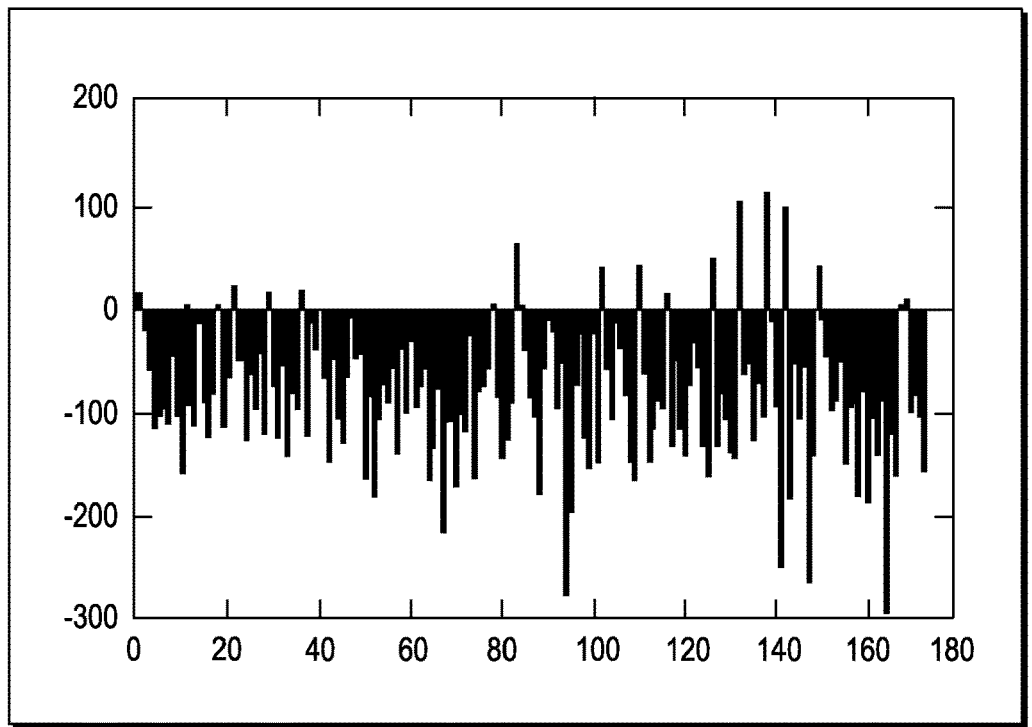
Figure 8C:
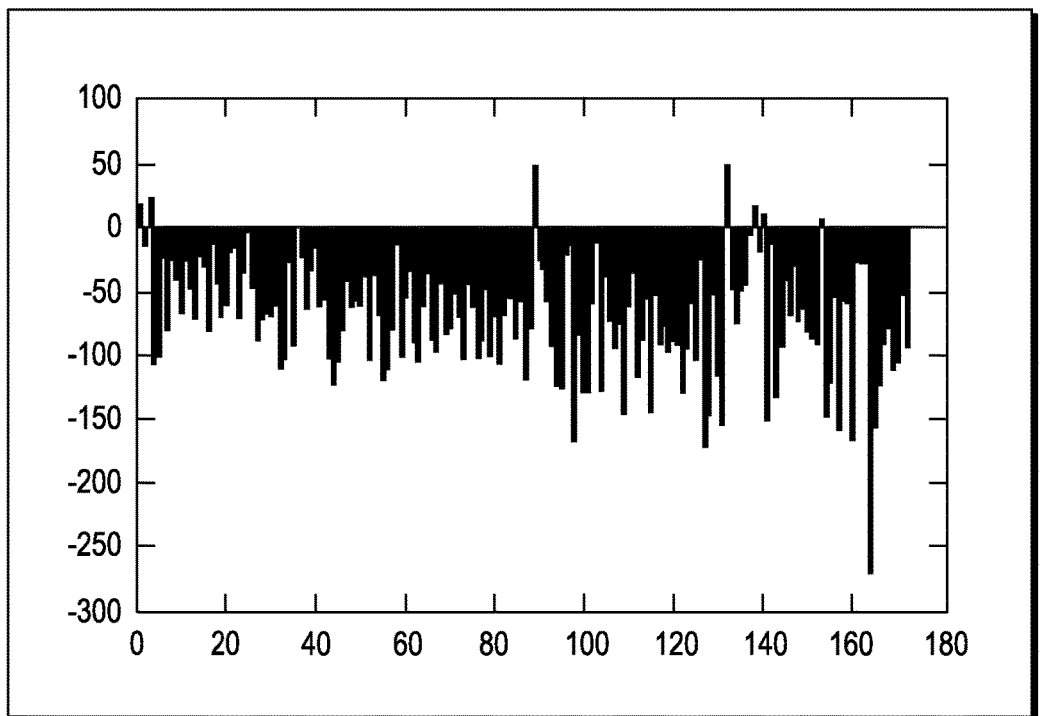
Figure 8D:
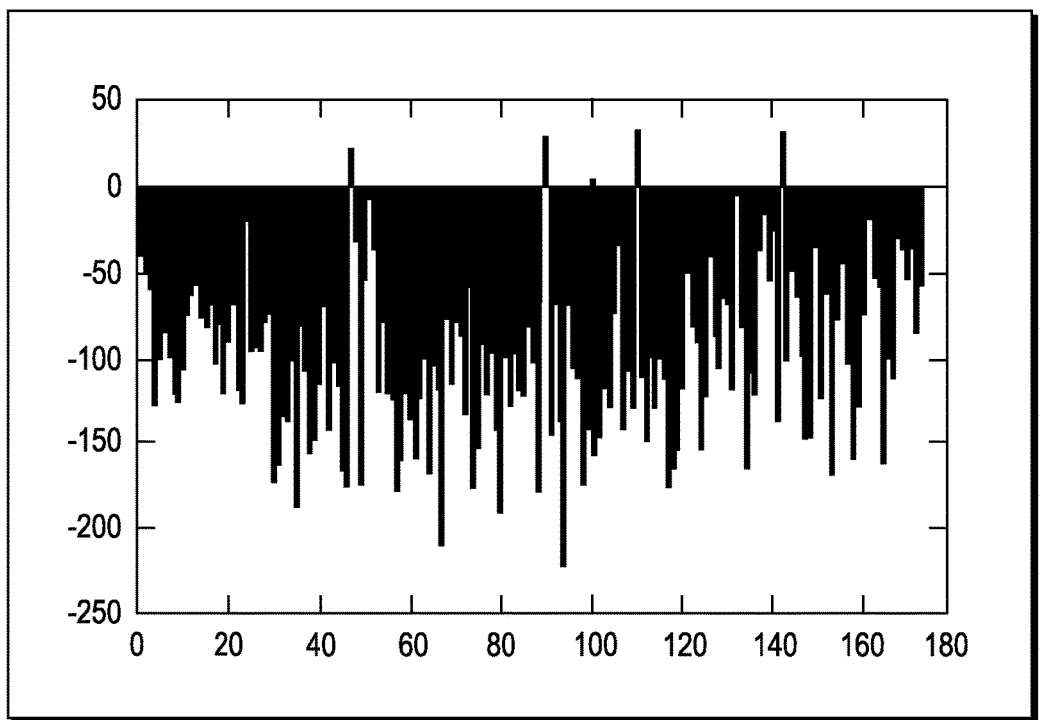
Figure 8E:
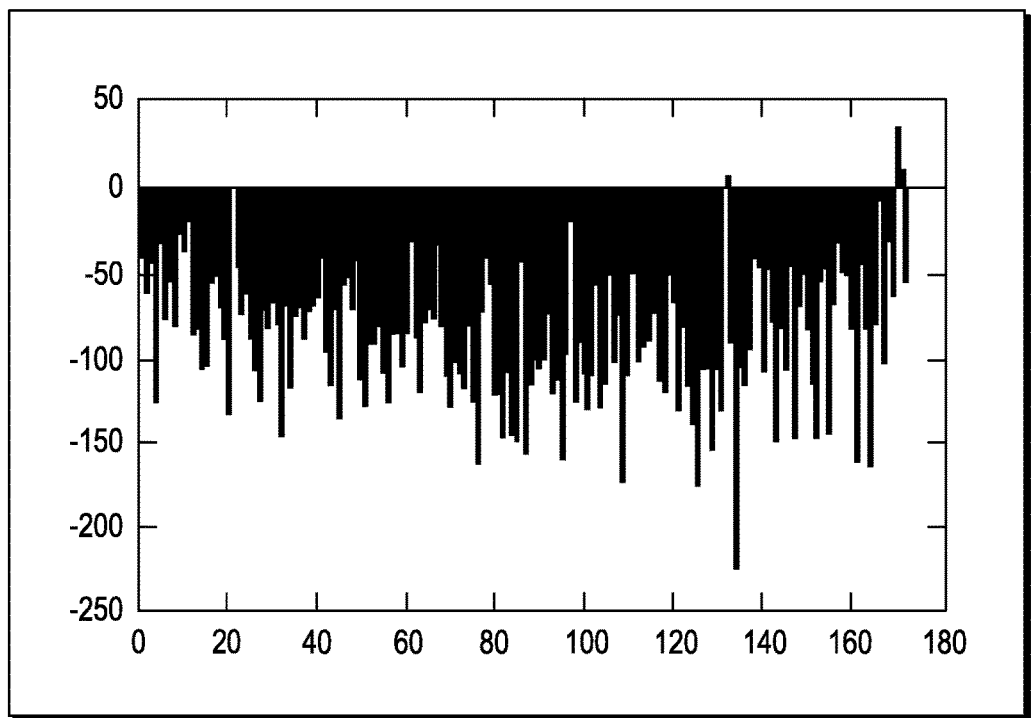
Figure 8F:
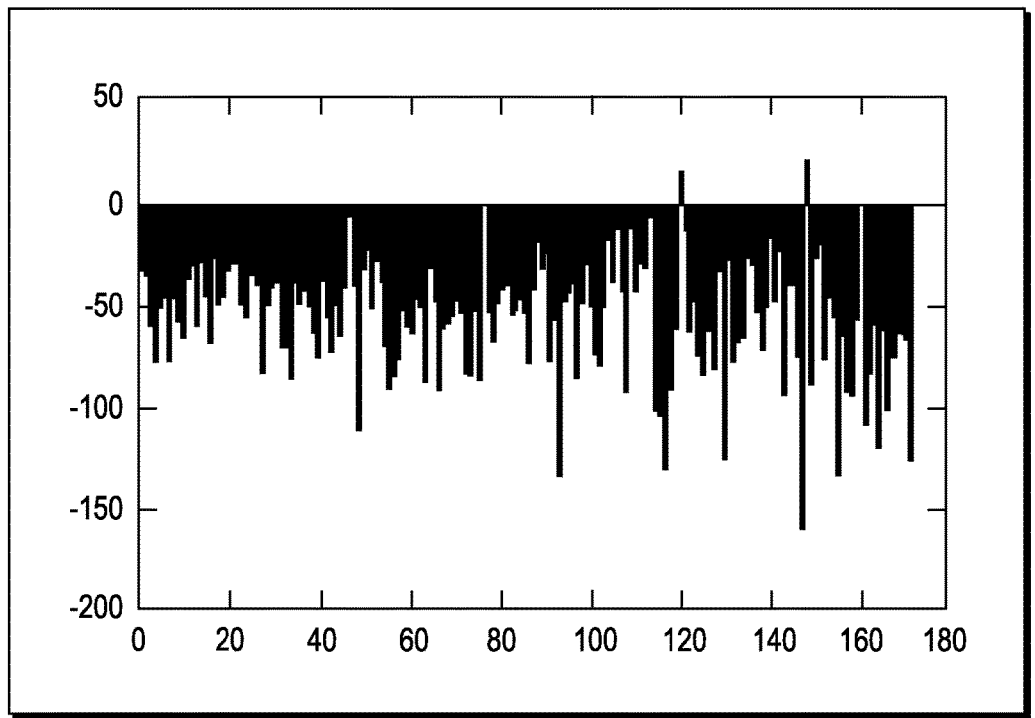
Figures 8G, 9:
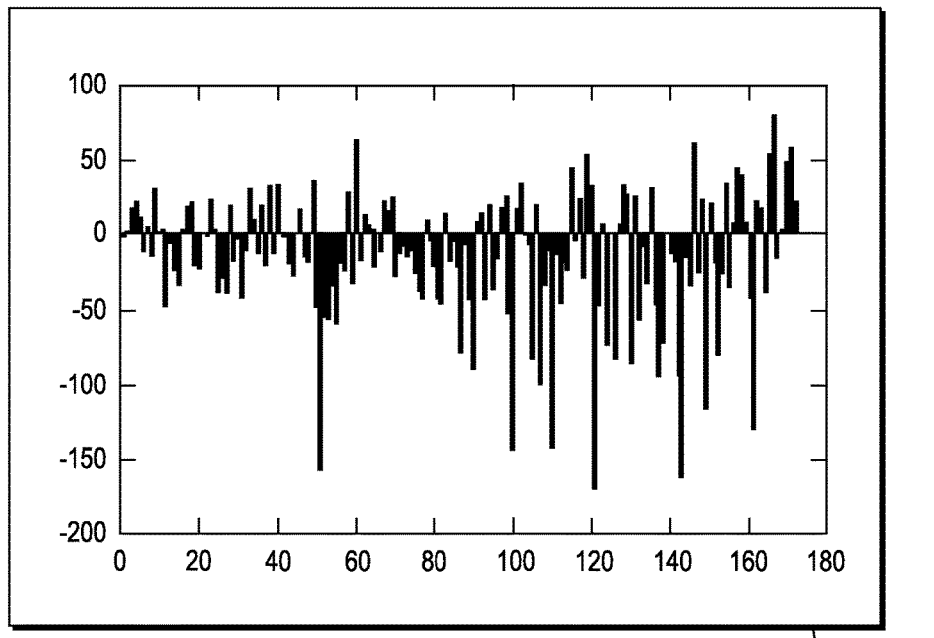
FIG. 9 is a table showing disease prediction accuracy percentages.

Disease prediction accuracy percentage is also shown in FIG. 9. Results from the proposed method "Subflow Dictionary" and a baseline method "Longest Common Subflow" are presented. In a given row; (i) the Control number is the accuracy of the system on cases without the disease; (ii) the Diseased number is the accuracy of cases with disease; and (iii) Mean is the average of the previous two accuracy numbers. The higher the number, the better the system. The proposed method can predict disease with over a 75% accuracy rate, on average.

In conclusion, echocardiogram workflows are known to be important, as is evident from various guidelines that present modality-viewpoint sequence protocols for investigating various diseases. But never before has the echocardiogram workflow data been explored for unknown and unseen patterns that are indicative of diseases. In this disclosure, one of the first attempts to exploit these hidden patterns for obtaining quick diagnostic insights into echocardiograms without looking into the image content is presented.

In addition to predicting presence of diseases, our method can also produce evidence to support its opinion. For instance, if a workflow is classified to have Aortic Stenosis, we could use the highest ranking subflows that are present in the disease discriminative model (FIG. 6) for Aortic Stenosis that are also present in the given workflow as evidence. Thus, the presented disease models are not mere black-box classifiers. For example, when software according to the present invention predicts a particular disease based on workflow analysis, the prediction is based on the observed fact that certain subflows (prominently present in the workflow) are indicative of that particular disease. Thus the prominent and indicative subflows can be specifically identified as evidence why it has been concluded that a particular workflow is indicative of a disease.

The current results of this method are encouraging, but at the same time, our findings suggest various other tantalizing directions for further investigation. For instance, the subflows that are often used in diagnosing large number of diseases could possible be made part of the standard practice guidelines. If appropriate labels are available, one could also use the proposed mechanism to obtain insight into how different subflows correlate with age, gender, or other physical conditions of the patients. Workflow descriptions obtained from sonographer trainees can be used to detect subflow patterns that are commonly used in error and can be explicitly corrected for. If viewpoint information is available, the workflow could be described in more detail and could possibly obtain higher accuracy rates.

From the data mining point of view, each disease is treated independently. Looking at the correlation between workflows of multiple diseases can further bolster the disease detection accuracy. Also, the current dictionary based representation of the workflows could be used to carry out unsupervised statistical analysis on the space of all workflows. This could possibly allow a visualization of workflows in 2D or 3D space.

It is important to not look at workflow based disease prediction as an alternative to actual medical image analysis. Workflow based prediction provides information complementary to what is present in the images and can be used to improve the performance of more detailed disease prediction systems. To conclude, it is important to reiterate that in this disclosure, examples have been presented, from a few first sorties, into the yet unexplored universe of echocardiography workflow mining. Models have been built, with reasonably high accuracy that can predict diseases without looking into an echocardiogram's image content. This method does not use any clinical measurements, rather predicts based on workflow. Workflow patterns are mined that predict outcomes (diseases) and not rules.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Software storage device: any device (or set of devices) capable of storing computer code in a manner less transient than a signal in transit.

Tangible medium software storage device: any software storage device (see Definition, above) that stores the computer code in and/or on a tangible medium.

Non-transitory software storage device: any software storage device (see Definition, above) that stores the computer code in a non-transitory manner.

Computer: any device with significant data processing and/or machine readable instruction reading capabilities including, but not limited to: desktop computers, mainframe computers, laptop computers, field-programmable gate array (fpga) based devices, smart phones, personal digital assistants (PDAs), body-mounted or inserted computers, embedded device style computers, application-specific integrated circuit (ASIC) based devices.

What is claimed is:

1. A method comprising:
receiving a plurality of machine logic based condition indication rules for a large-scale medical data mining program, with each given condition indication rule of the plurality of condition indication rules including: (i) a qualifying workflow corresponding to an ordered series of medical examination related operations, and (ii) a consequential portion corresponding to information indicative of a potential health status or condition; and
mining, by the software of the large-scale medical data mining program, a plurality of N medical workflow data sets by:
receiving a first medical workflow data set of the plurality of N medical workflow data sets including information indicative of a first workflow defined by: (i) an ordered series of medical examination related operations performed on a first subject, and (ii) a plurality of modalities generated by a first magnetic resonance imaging (MRI) machine,
determining that a qualifying workflow of a first condition indication rule of the plurality of machine indication rules is a match with the: (i) ordered series of medical examination related operations performed on the first subject, and (ii) the plurality of modalities generated by the first magnetic resonance imaging (MRI) machine of the first workflow, responsive to the determination that the qualifying workflow of the first condition indication rule is a match with the first workflow, applying, by machine logic of the large-scale medical data mining program, the first condition indication rule to determine that the consequential portion of the first condition indication rule is potentially applicable to the first subject, receiving an N-th medical workflow data set of the plurality of N medical workflow data sets including information indicative of an N-th workflow defined by an ordered series of medical examination related operations performed on a first subject, determining that a qualifying workflow of a N-th condition indication rule of the plurality of machine indication rules is a match with the N-th workflow, responsive to the determination that the qualifying workflow of the N-th condition indication rule is a match with the N-th workflow, applying, by machine logic of the large-scale medical data mining program, the N-th condition indication rule to determine that the consequential portion of the N-th condition indication rule is potentially applicable to the first subject, and communicating, to a health care professional, the determination that the consequential portion of the N-th condition indication rule is potentially applicable to the first subject.

2. The method of claim 1 further comprising:
determining, by a human expert, the first condition indication rule.

3. The method of claim 1 wherein the first workflow is defined by a plurality of modalities that are generated by a first ultrasound machine.

\* \* \* \* \*